United States Patent [19]

Hogle et al.

[11] Patent Number: 5,637,708

[45] Date of Patent: Jun. 10, 1997

[54] STRUCTURE BASED DESIGN OF CAPSID STABILIZING OR ANTIVIRAL AGENTS

[75] Inventors: James M. Hogle, Newtonville; Martin Karplus, Cambridge; Diane Joseph-McCarthy, Belmont, all of Mass.

[73] Assignee: President and Fellows of Harvard College, Cambridge, Mass.

[21] Appl. No.: 460,113

[22] Filed: Jun. 2, 1995

Related U.S. Application Data

[63] Continuation of Ser. No. 207,411, Mar. 7, 1994, abandoned.

[51] Int. Cl.$^6$ .................................................. C07D 401/02
[52] U.S. Cl. ...................... 546/140; 546/148; 548/305.4; 548/457
[58] Field of Search ..................................... 546/140, 148; 548/190, 305.4, 457

[56] References Cited

U.S. PATENT DOCUMENTS

| | | | |
|---|---|---|---|
| 4,843,087 | 6/1989 | Diana et al. | 514/374 |
| 4,857,539 | 8/1989 | Diana et al. | 514/378 |
| 4,861,791 | 8/1989 | Diana et al. | 514/374 |
| 4,939,267 | 7/1990 | Diana et al. | 548/237 |
| 4,992,433 | 2/1991 | Stokbroekx et al. | 514/212 |
| 5,070,090 | 12/1991 | Stokbroekx et al. | 514/236.5 |
| 5,175,177 | 12/1992 | Diana et al. | 514/364 |

OTHER PUBLICATIONS

Pickholtz et al, Tetrahedron Letters, No.14, 1974, pp. 1263–1266.
Guilani et al, J. of Heterocyclic Chem, vol. 27, No. 4, May–Jun., 1990, pp. 1007–1009.
Al–Nakib, W., et al., "Suppression of Colds in Human Volunteers Challenged with Rhinovirus by a Synthetic Drug (R61837)," *Antimicrobial Agents and Chemotherapy*, 33(4):522–525 (1989).
Andries, K., et al., "In Vitro Activity of Pirodavir (R 77975), a Substituted Phenoxy–Pyridazinamine with Broad–Spectrum Antipicornaviral Activity," *Antimicrobial Agents and Chemotherapy*, 36(1):100–107 (1992).
Andries, K., et al., "In vitro Activity of R 61837, A New Antirhinovirus Compound," *Archives of Virology*, 101:155–167 (1988).
Andries, Koen, et al., "Two Groups of Rhinoviruses Revealed by a Panel of Antiviral Compounds Present Sequence Divergence and Differential Pathogenicity," *Journal of Virology*, 64(3):1117–1123 (1990).
Badger, John et al., "Structural Analysis of Antiviral Agents That Interact With the Capsid of Human Rhinoviruses," *Proteins: Structure, Function, and Genetics*, 6:1–19 (1989).
Badger, John, et al., "Structural Analysis of a Series of Antiviral Agents Complexed with Human Rhinovirus," *Proc. Natl. Acad. Sci. USA*, 85:3304–3308 (1988).
Badger, John, et al., "Three dimensional Structures of Drug–resistant Mutants of Human Rhinovirus 14," *J. Mol. Biol.*, 207:163–174 (1989).

Bailey, Thomas R., et al., "Antirhinoviral Activity of Heterocyclic Analogys of Win 54954," *J. Med. Chem.*, 35:4628–4633 (1992).
Chapman, Michael S., et al., "Human Rhinovirus 14 Complexed with Aniviral Compound R 61837," *J. Mol. Biol.*, 217:455–463 (1991).
Diana, Guy D., et al., "Inhibitors of Viral Uncoating," *Pharmac. Ther.*, 42:289–305 (1989).
Diana, Guy D., et al., "Synthesis and Structure–Activity Studies of Some Disubstituted Phenylisoxazoles against Human Picornavirus," *J. Med. Chem.*, 32:450–455 (1989).
Diana, Guy D., et al., "A Model for Compounds Active against Human Rhinovirus–14 Based on X–ray Crystallography Data," *J. Med. Chem.*, 33:1306–1311 (1990).
Diana, Guy D., et al., "CoMFA Analysis of the Interactions of Antipicornavirus Compounds in the Binding Pocket of Human Rhinovirus–14," *J. Med. Chem.*, 35:1002–1008 (1992).
Fox, M. Patricia, et al., "Prevention of Rhinovirus and Poliovirus Uncoating by WIN 51711, A New Antiviral Drug," *Antimicrobial Agents and Chemotherapy*, 30(1):110–116 (1986).
Fox, M. Patricia, et al., "Binding Affinities of Structurally Related Human Rhinovirus Capsid–Binding Compounds Are Related to Their Activities against Human Rhinovirus Type 14," *Antimicrobial Agents and Chemotherapy*, 35(6):1040–1047 (1990).
Gruenberger, Martin, et al., "Stabilization of Human Rhinovirus Serotype 2 against pH–induced Conformational Change by Antiviral Compounds," *Journal of General Virology*, 72:431–433 (1991).
Heinz, Beverly A., et al., "Genetic and Molecular Analyses of Spontaneous Mutants of Human Rhinovirus 14 That Are Resistant to an Aniviral Compound," *Journal of Virology*, 63(6):2476–2485 (1989).
Kim, Sangsoo, 35 al., "Crystal Structure of Human Rhinovirus Serotype 1A (HRV1A)," *J. Mol. Biol.*, 210:91–111 (1989).

(List continued on next page.)

Primary Examiner—Zinna Northington Davis
Attorney, Agent, or Firm—Hamilton, Brook, Smith & Reynolds, P.C.

[57] ABSTRACT

Agents having the structure,

U—CH$_2$—V—CH$_2$—W, and agents having the structure,

U—CH$_2$—V—CH$_2$—W—X—Y—Z, where U, W, and Z are double fused aromatic rings, V is a single six-membered aromatic ring with a hydroxyl group constituent, X is a polar group, and Y is a positively charged group, are disclosed. The double fused aromatic rings can be a five-membered aromatic ring, or a six-membered aromatic ring, fused to a six-membered aromatic ring; the double fused aromatic rings can comprise heteroatoms. The agents can be used as capsid stabilizing or antiviral agents.

1 Claim, 25 Drawing Sheets

OTHER PUBLICATIONS

McKinlay, Mark A., et al., "Treatment of the Picornavirus Common Cold By Inhibitors of Viral Uncoating and Attachment," *Annu. Rev. Microbiol.*, 46:635–54 (1992).

McSharry, James J., et al., "Inhibition of Uncoating of Poliovirus by Arildone, a New Antiviral Drug," *Virology* 97:307–315 (1979).

Moereman, Marc, et al., "Study of the Parameters of Binding of R 61837 to Human Rhinovirus 9 and Immunobiochemical Evidence of Capsid Stabilizing Activity of the Compound," *Antimicrobial Agents and Chemotherapy*, 36(2):417–424 (1992).

Peters, Richard, et al., "Three–Dimensional Modeling and Drug Development," *Biotechnology*, 12:147–150 (Feb., 1994).

Pevear, Daniel C., et al., "Conformational Change in the Floor of the Human Rhinovirus Canyon Blocks Adsorption to HeLa Cell Receptors," *Journal of Virology*, 63(5):2002–2007 (1989).

Rossmann, Michael G., et al., "Antiviral Agents Targeted to Interact with Viral Capsid Proteins and Possible Application to Human Immunodeficiency Virus," *Proc. Natl. Acad. Sci. USA*, 85:4625–4627 (1988).

Rossmann, Michael G., et al., "The Structure of Antiviral Agents that Inhibit Uncoating when Complexed with Viral Capsids," *Antiviral Research*, 11:3–14 (1989).

Smith, Thomas J., et al., "The Site of Attachment in Human Rhinovirus 14 for Antiviral Agents That Inhibit Uncoating," *Research Articles*, 233:1286–1293 (1986).

Woods, M.G., et al., "In Vitro and In Vivo Activities of WIN 54954, a New Broad–Spectrum Antipicornavirus Drug," *Antimicrobial Agents and Chemotherapy*, 33(12):2069–2074 (1989).

Caliguiri, Lawrence A., et al., "Effect of Arildone on Modifications of Poliovirus In Vitro," *Virology*, 105:86–93 (1980).

Zhang, Angiang, et al., "Three–dimensional Structure–activity Relationship for Antiviral Agents that Interact with Picornavirus Capsids," *Virology*, 3:453–471 (1992).

Rajeswaran, W. G. and Srinivasan, P. C., "A Convenient Synthesis of 2–Arylmethylindoles," *Synthesis*, 835–836 (Sep. 1992).

Roderick, William, R., et al. "Bisbenzimidazoles Potent Inhibitors of Rhinoviruses,"*Journal of Medicinal Chemistry*, 15(6):655–658 (1972).

Walselman, M., et al., "Nucleophilic Displacement of Hydroxybenzyl Halides by Indoles in Aqueous Medium," *Chemical Abstracts*, 69(2):1089–1091 (1968).

Decodts, G., et al., "Alkylation of Indoles with Hydroxymethyl–amino–methyla and (halomethyl) (phenols)," *Tetrahedron*, 26(13):3313–28 (1970).

Fused double aromatic rings (either a 5-membered and 6-membered or two 6-membered rings), possibly with substituted heteroatoms.

Single 6-membered aromatic ring with hydroxyl group substituent.

Fused double aromatic rings (either a 5-membered and 6-membered or two 6-membered rings), possibly with substituted heteratoms.

STRUCTURE BASED DESIGN OF CAPSID STABILIZING OR ANTIVIRAL AGENTS

RELATED APPLICATION

This application is a continuation of application Ser. No. 08/207,411 filed Mar. 7, 1994, now abandoned, which is incorporated herein by reference in its entirety.

GOVERNMENT SUPPORT

This invention was supported by NIH Grant Nos. AI32480, AI20566 and GM39589 and the United States Government has certain rights to this invention.

BACKGROUND OF THE INVENTION

Poliovirus is a member of the picornaviruses, a large family of small ribonucleic acid-containing viruses responsible for many serious human and animal diseases (Rueckert, R. R. *Virology*, 2nd ed. (Field, B. N. et al., eds.) Raven Press, Ltd., New York, p. 508–548 (1982)). Two genera of the picornavirus family are enteroviruses, which include poliovirus and Coxsackievirus, and rhinoviruses. Poliovirus is the etiologic agent of the disease poliomyelitis in humans, and there are three known serotypes of the virus. The oral poliovaccine, typically given to children, is a mixture of the Sabin strain of the three serotypes of the virus. Mahoney and Leon (the parent strains of Sabin 1 and 3, respectively) are human neurovirulent strains of poliovirus. The oral poliovirus vaccine is safe and effective, yet has two limitations. First, the vaccine is unstable; current vaccines are inactivated by relatively brief (less than 24 hours) exposure to temperatures of 37° C., necessitating transport in a frozen state from the site of manufacture to the locale where they are administered. Second, the vaccine occasionally reverts to virulence in vaccine recipients; the reverted virulent virus may also be passed to other individuals who come into contact with the recipient in whom the vaccine has reverted. The human rhinoviruses consist of at least 100 serotypes and are the primary causative agents of the common cold. Because of the large number of serotypes, development of a vaccine is problematic; antiviral agents may therefore be the best approach to treatment. Other important members of the picornavirus family include human hepatitis A virus, Theiler's murine encephalomyelitis virus, foot-and-mouth disease virus, and mengovirus.

Several crystal structures of poliovirus and rhinovirus capsids have been solved by X-ray diffraction. The X-ray structures of poliovirus P1/Mahoney (Hogle, J. M., et al., *Science* 229:1358 (1985)); poliovirus P3/Sabin (Filman, D. J., et al., *EMBO J.* 8:1567 (1989)); rhinovirus 14 (Rossman, M. G., et al., *Nature* 317:145 (1985)); rhinovirus 1A (Smith, T. J., et al., *Science* 233:1286 (1986)); and rhinovirus 16 (Oliveira, M. A., et al., *Structure* 1(1):51–68 (1993)) are strikingly similar, although poliovirus and the rhinoviruses are currently classified in different genuses. From experiment, it is known that there is a binding site in the poliovirus structure which usually binds a lipid-like molecule (Filman, D. J., et al., *EMBO J.* 8:1567 (1989)). When a drug is bound in this site, the virus is stabilized, and in some cases, infection is prevented (McSharry, J. J., et al., *Virology* 97:307 (1979); Smith, T. J., et al., *Science* 233:1286 (1986); reviewed in Zhang, A., et al., *Virology*, 3:453 (1992) ).

The existing drugs against these viruses are only moderately effective. Available drugs are typically effective against a limited subset of the rhinovirus serotypes. In addition, the drugs have either failed to demonstrate sufficient prophylactic effect or are converted in the body into inactive metabolites. Furthermore, current drugs have all been derived from the same parent compound that was found through large-scale random screening of known chemicals for activity against the virus, a very expensive and time-consuming process. A need continues for additional drugs with better efficacy, and with efficacy against several viruses.

SUMMARY OF THE INVENTION

The current invention pertains to capsid stabilizing or antiviral agents, having a general structure known as a "core" region. The core region consists of three functional groups: a fused double aromatic ring group (U), which consists of either a five- or a six-membered aromatic ring fused to a six-membered aromatic ring; a single six membered aromatic ring (V) which can optionally have a hydroxyl group substituent on any of the available ring atoms; and a second fused double aromatic ring (W), which also consists of either a five- or a six-membered aromatic ring fused to a six-membered aromatic ring. The first fused double aromatic ring (U), the second fused double aromatic ring (W), or both of the fused double aromatic rings (U and W), can have heteroatoms substituted for carbon atoms. These three functional groups are connected by single linker carbon atoms, such that the core region has the general structure:

$$U—CH_2—V—CH_2—W.$$

The agent may additionally have a "tail" region connected to the core region. The tail region also consists of three functional groups: a polar group (X) with an oxygen atom, a positively charged group (Y), and a fused double aromatic ring (Z), which may be either a five- or a six-membered aromatic ring fused to a six-membered aromatic ring. The fused double aromatic ring can have heteroatoms substituted for carbon atoms. The positively charged group can be, for example, an ammonium group. These three functional groups are arranged such that the tail region has the general structure:

$$X—Y—Z.$$

If such a tail region is present, it is connected to the core region such that the overall structure of the agent is:

$$U—CH_2—V—CH_2—W—X—Y—Z.$$

Any of the functional groups can have additional small groups attached, such as, for example, alkyl groups (such as methyl groups) halides, hydroxyl groups or amino groups.

The agents were designed through the use of new computational technologies, which allowed the "mapping" of the drug binding site in the virus of interest, including the localization of functional groups within the binding site. The agents were specifically designed so that the functional groups have potential energy minima within the binding site.

The agents can be used to increase the thermal stability of the virus, and thereby formulate thermostable virus vaccines, making it possible to administer the vaccine to humans in areas of the world where refrigeration is prohibitively expensive. Furthermore, the agents which decrease the infectivity of the virus can also be used for early intervention in cases of poliomyelitis. Alternatively, the agents can be used to terminate excretion of virus in vaccinees after immune induction, as well as for prophylaxis in non-vaccinated individuals who might become infected by a vaccinee in whom the virus has reverted to virulent form. In addition, since previous studies have shown that capsid binding drugs generally have a broad spectrum of activity among entero/rhinovirus (Andriew, K. et al., *J. Virol.* 64:1117–1123 (1990)), it is reasonable to expect that agents which bind to one virus, such as poliovirus, will be effective against related viruses, such as rhinoviruses and Coxsackieviruses. The agents can also be used to stabilize an unstable form of a virus for experimental studies.

DETAILED DESCRIPTION OF THE INVENTION

The current invention pertains to a series of agents, depicted in FIGS. 2–6 and 14–20, which represent a new class of agents for stabilization of poliovirus and related viruses, and also for antiviral activity against poliovirus and related viruses. The agents were computationally based on several X-ray structures of poliovirus. A computer program was used to create functional (chemical) group maps of the Sabin 3 poliovirus binding site. Selected functional group minima were connected by energy minimization and dynamics to obtain agent molecules.

Figure 1:
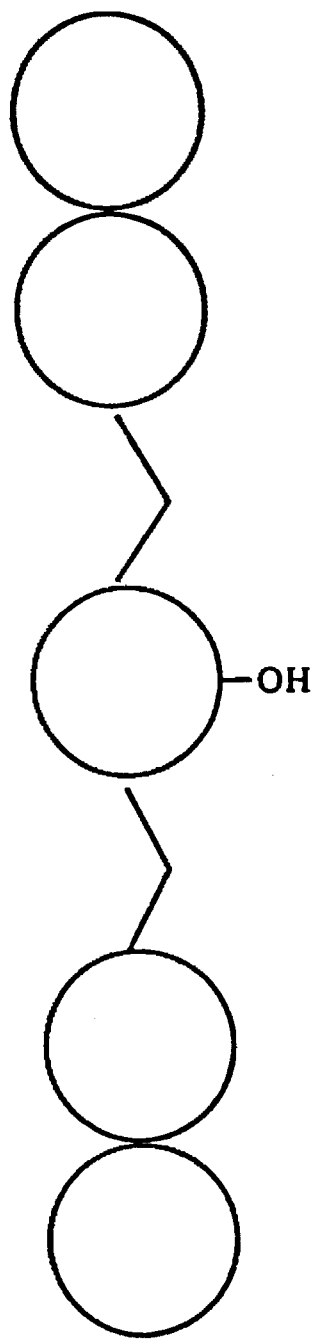
FIG. 1 is a depiction of the general structure of a core region of the agents of the current invention.
Figure 2:
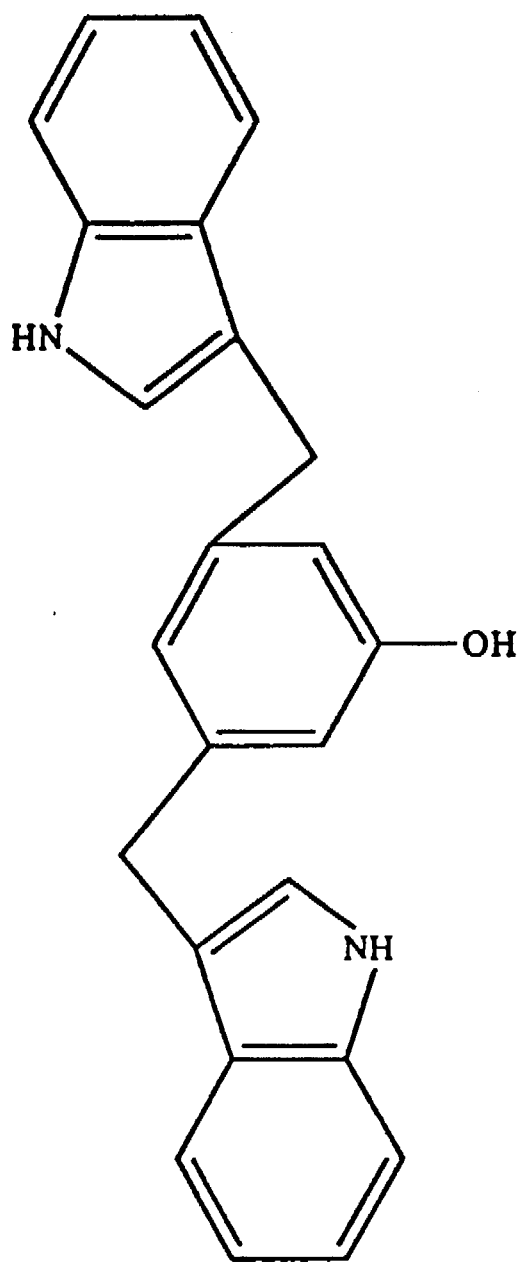
FIG. 2 is a depiction of a representative core region.
Figure 3:
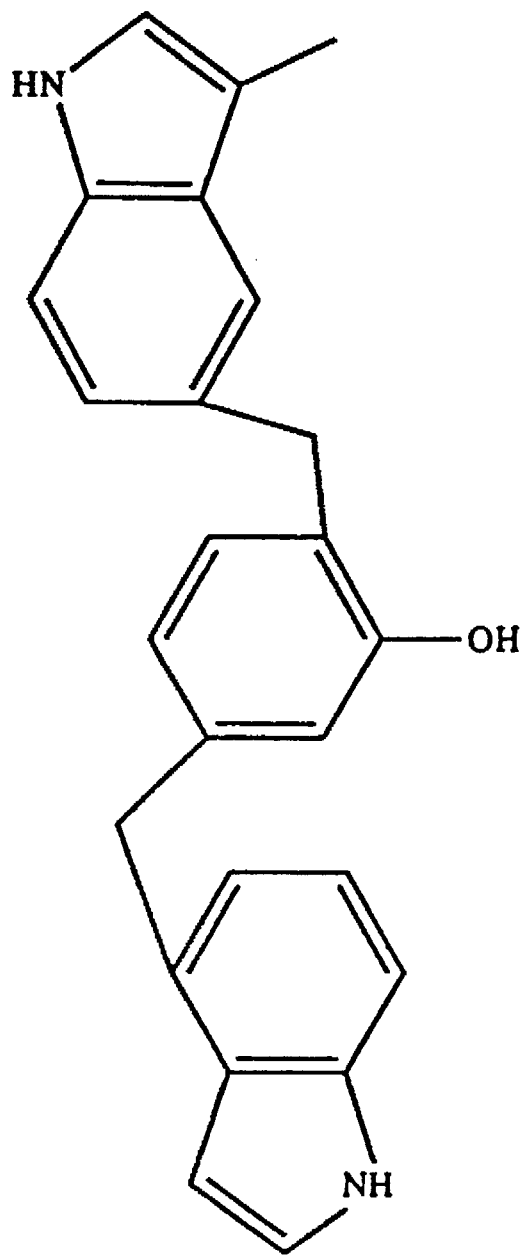
FIG. 3 is a depiction of a representative core region.
Figure 4:
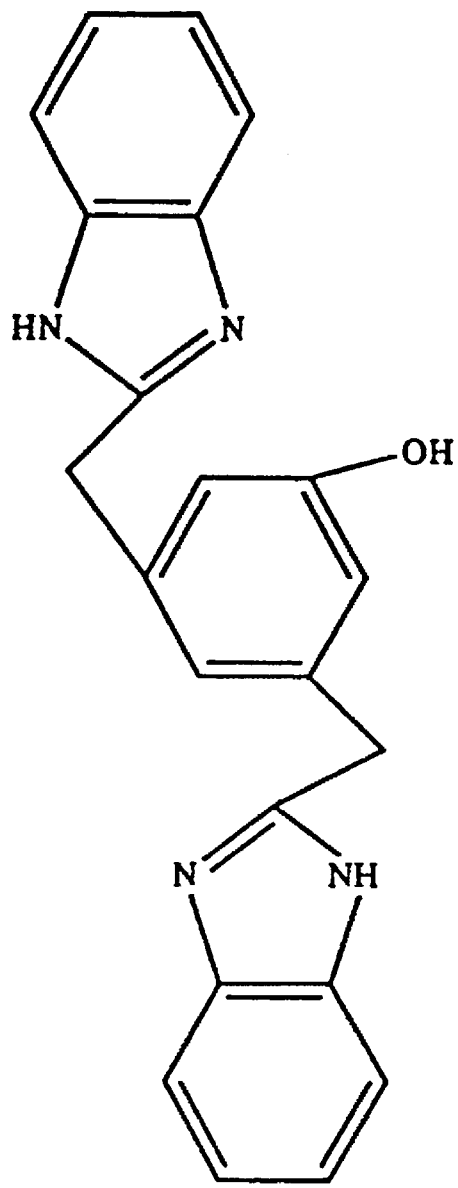
FIG. 4 is a depiction of a representative core region.
Figure 5:
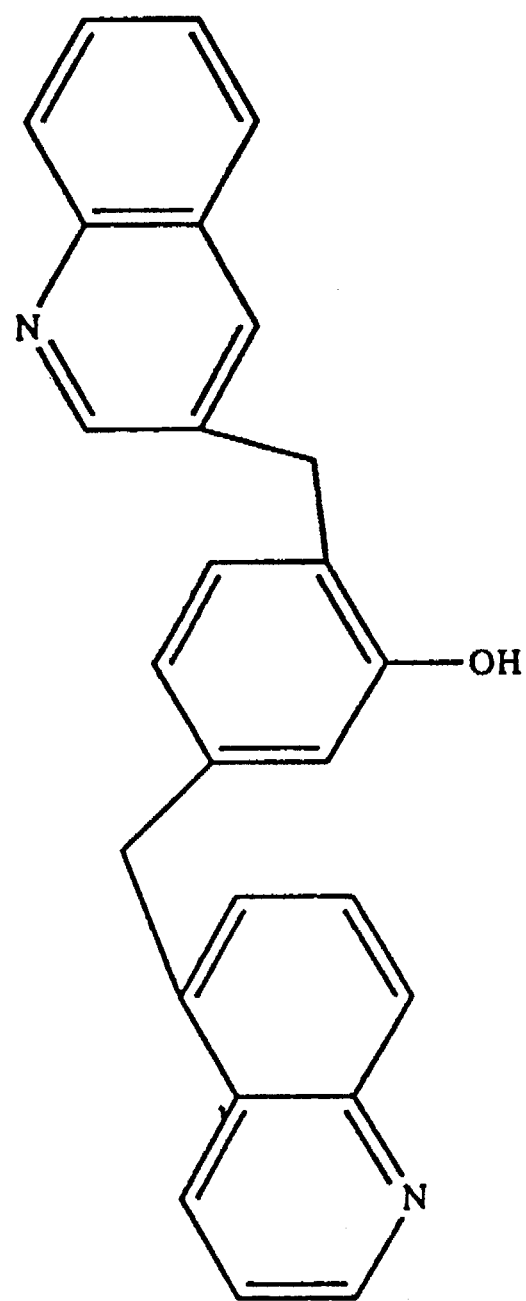
FIG. 5 is a depiction of a representative core region.
Figure 6:
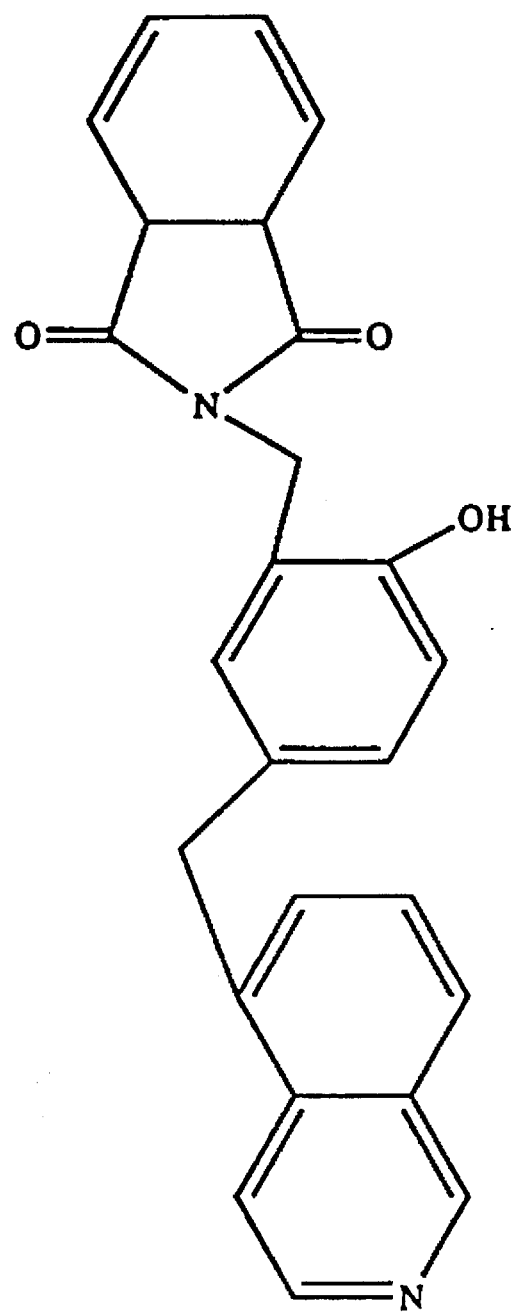
FIG. 6 is a depiction of a representative core region.
Figure 7:
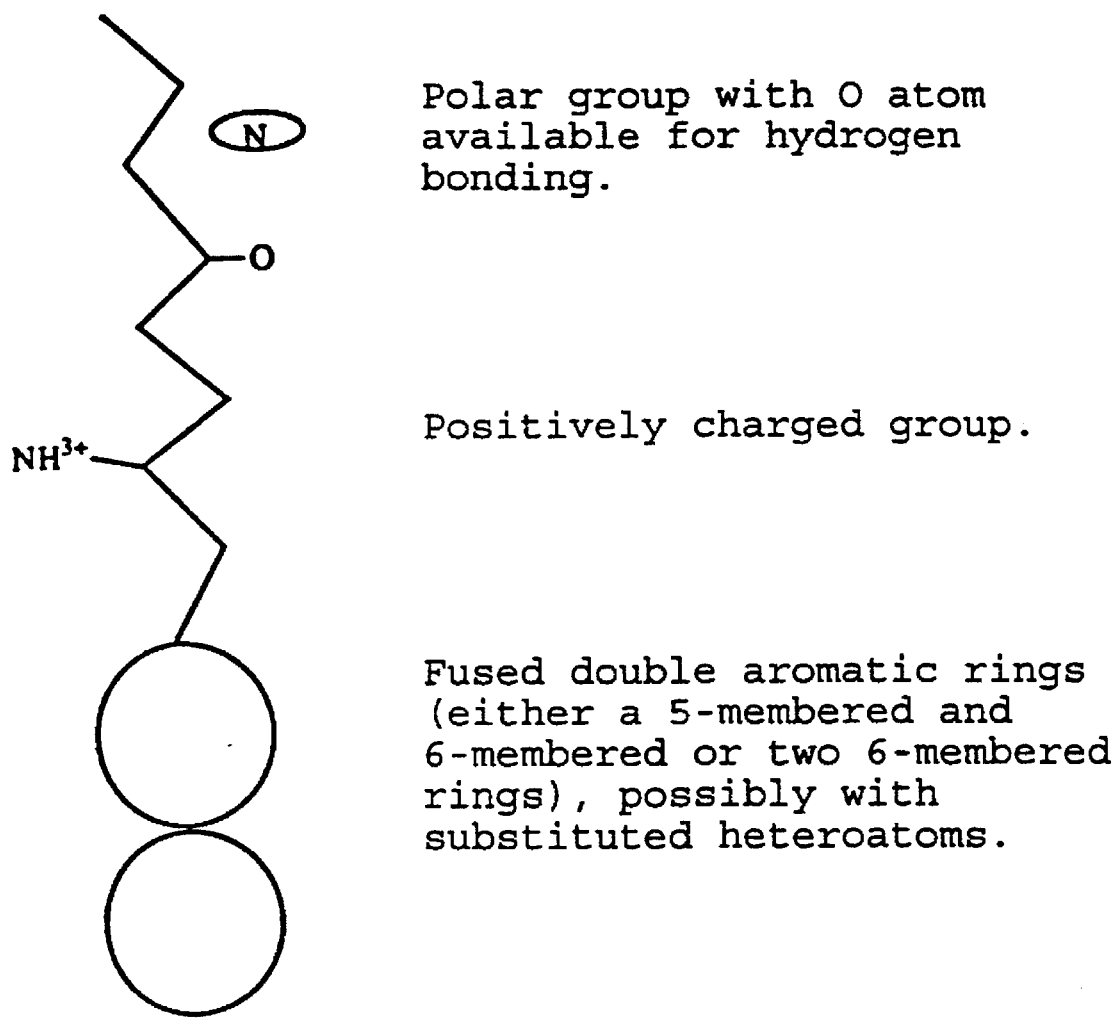
FIG. 7 is a depiction of the general structure of a tail region of the agents of the current invention.
Figure 8:
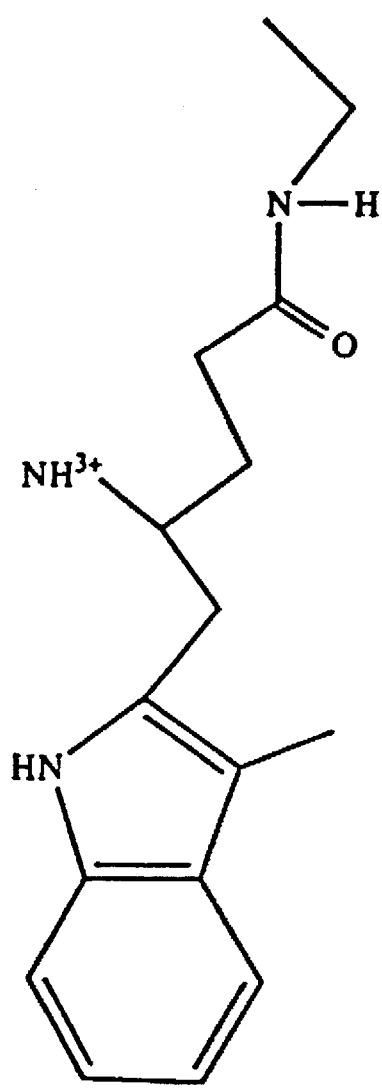
FIG. 8 is a depiction of a representative tail region.
Figure 9:
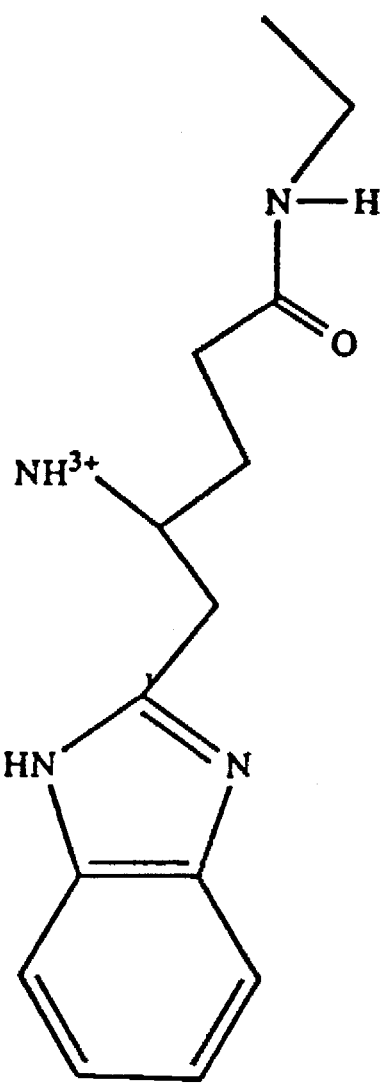
FIG. 9 is a depiction of a representative tail region.
Figure 10:
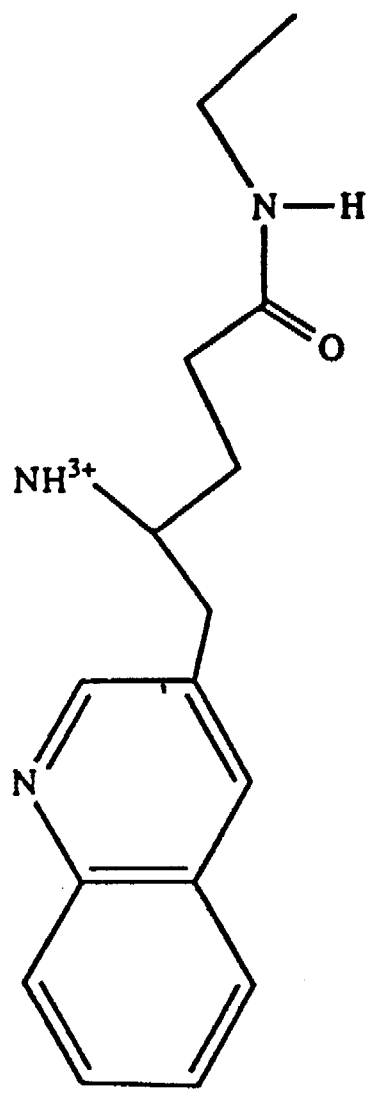
FIG. 10 is a depiction of a representative tail region.
Figure 11:
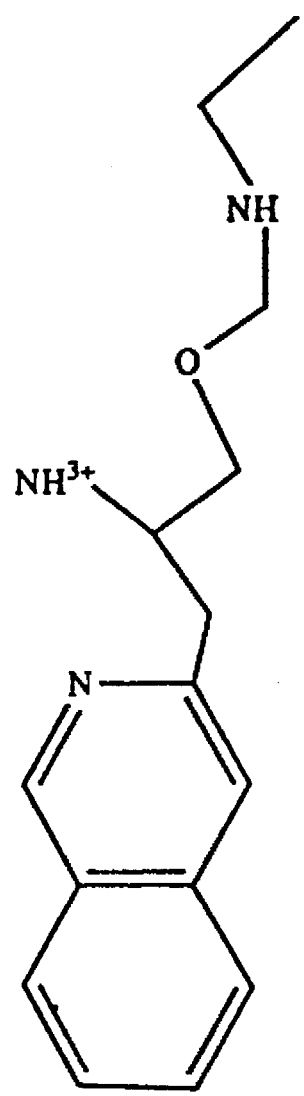
FIG. 11 is a depiction of a representative tail region.
Figure 12:
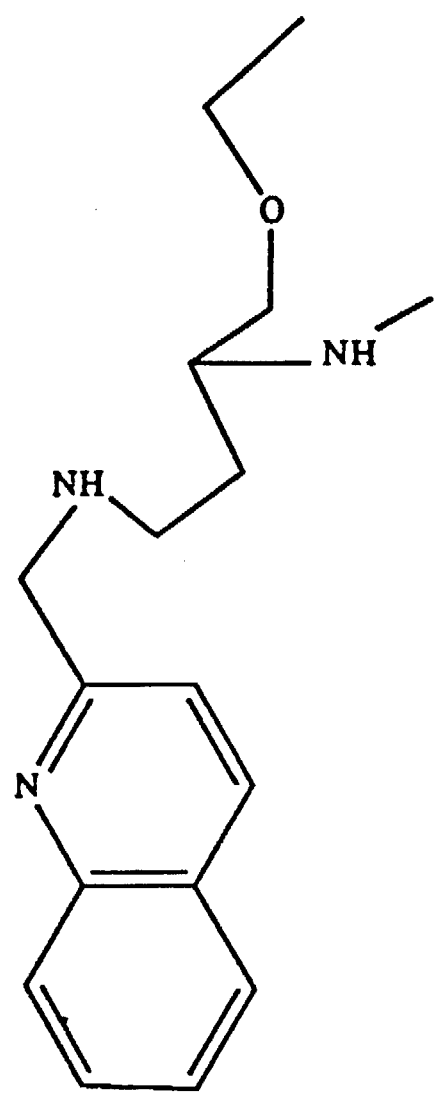
FIG. 12 is a depiction of a representative tail region.

The agents have a "core" region which fits deepest into the drug binding pocket of the virus, and can also have a more variable "tail" region. The general structure of the core region is depicted in FIG. 1, and the general structure of the tail region is depicted in FIG. 7. The unique features of the core region are two fused double aromatic rings (U and W), which consist of either a five-membered aromatic ring fused to a six-membered aromatic ring, or two six-membered aromatic rings fused to one another; and a single six membered ring (V) which optionally can have a hydroxyl group substituent on any of the available ring atoms. The two fused double aromatic rings are connected by single linker carbons, such that the core region has the structure:

$$U-CH_2-V-CH_2-W.$$

One or more atoms in the two fused double aromatic rings can be heteroatoms (nitrogen or oxygen), substituted for carbon atoms. Examples of core regions of agents of the current invention are shown in FIGS. 2–6. The core region occupies most of the drug binding site.

The features of the tail region include a polar group (X) having an oxygen atom, a positively charged group (Y), and a bulky fused double aromatic ring structure (Z) at the end, which consists of either a five-membered aromatic ring fused to a six-membered aromatic ring, or two six-membered aromatic rings fused to one another. This fused double aromatic ring may have one or more heteroatoms (nitrogen or oxygen) substituted for carbon atoms. Both the polar group (X) and the positively charged group (Y) interact with the protein. In one embodiment of the current invention, the positively charged group is an ammonium group. These functional groups are arranged such that the tail region has the structure:

$$X-Y-Z.$$

The tail region extends out of the drug binding site into the receptor binding site.

If a tail region is present, it is connected to the core region by a covalent linkage (such as a methylene or chain of methylenes) such that the fused double aromatic ring W is connected to polar group X. The structure of an agent having both a core region and a tail region is:

$$U-CH_2-V-CH_2-W-X-Y-Z.$$

Figure 13:
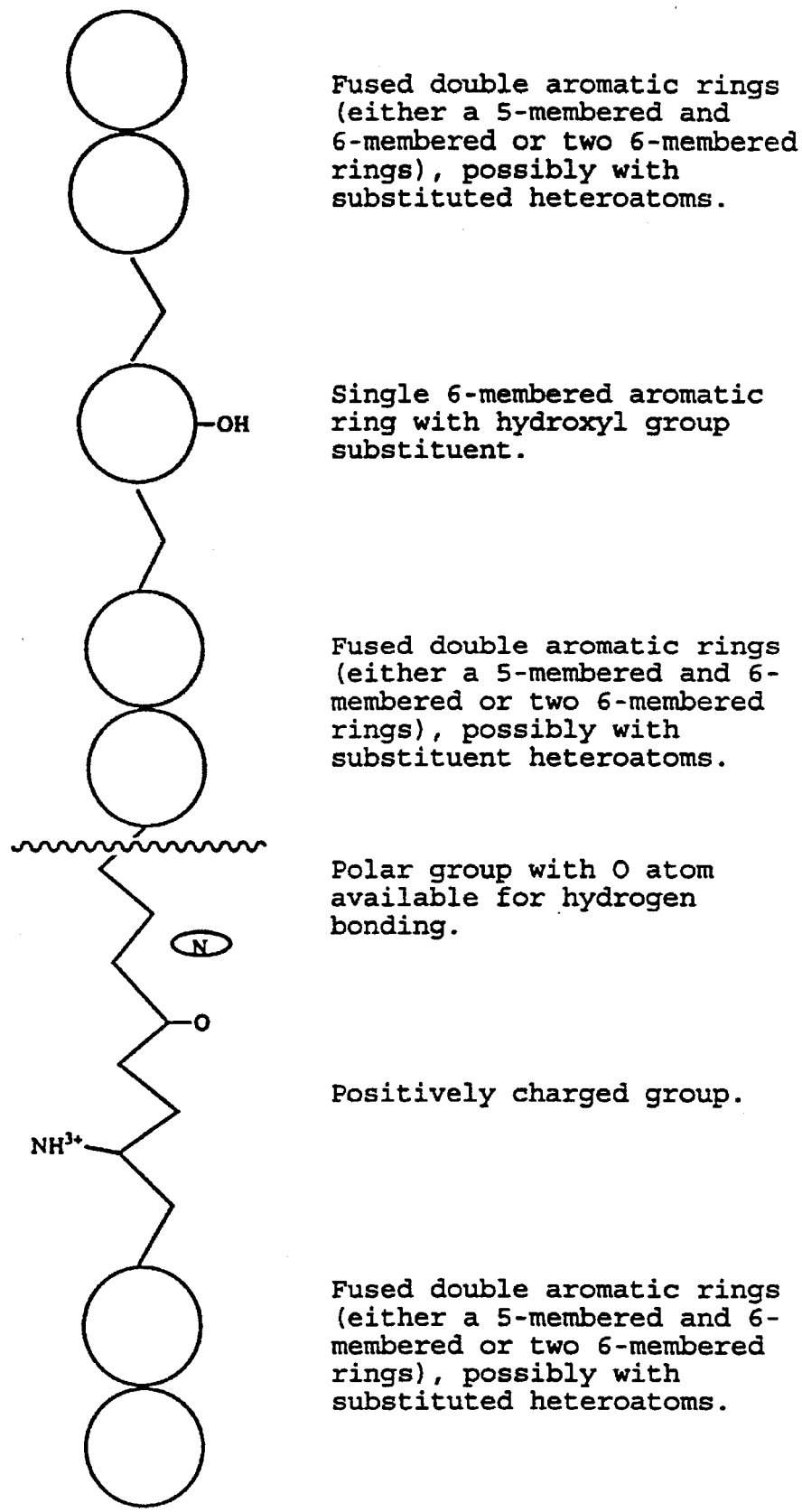
FIG. 13 is a depiction of the general structure of agents of the current invention in which the core region is connected to a tail region.

FIG. 13 depicts the general structure of an agent having a core region and a tail region. Examples of such agents are shown in FIGS. 14–20.

Any of the functional groups (U, V, W, X, Y, and/or Z) can additionally have small groups attached. Such groups include alkyl (such as methyl [—$CH_3$]) groups; halides (such as fluorine or chlorine); hydroxyl (—OH) groups; or amino (—$NH_2$) groups.

The fused double aromatic rings at either end of the core region in these agents are not present in any currently existing antipicornavirus drugs; furthermore, they are more rigid and compact than the groups which are present in the other drugs. A striking difference between these agents and existing drugs is the placement of a bulky group at the center of the binding pocket, specifically the phenol group between the two fused double aromatic rings of the core region. In addition, the presence of a relatively long tail region is in itself unique.

The agents of the current invention were designed using computational methods. Computational agent design can be thought of as a three step process. First, the localization of specific functional (chemical) groups in the binding site is calculated, such that the groups have potential energy minima. Second, the resulting functional group minima are clustered and connected to design new ligands or agents for the binding pocket. Third, the binding constants of new ligand are estimated to predict how tightly the ligand will bind.

In an example of computational agent design (described in further detail in Example 2 below), the Multiple Copy Simultaneous Search (MCSS) program (Miranker, A. and Karplus, M., *Proteins*, 11:29 (1991)) has been used to "map" the agent binding site of poliovirus. This work was the first application of MCSS for designing non-peptide ligands. The resulting minima were clustered and connected to form two new agents for poliovirus, shown in FIGS. 14 (Agent A) and 15 (Agent B).

The agents of the current invention can be used to stabilize capsids of picornaviruses and other related viruses by contacting the virus with the agent. The agents can thus be used to stabilize unstable forms of virus for experimental studies. The agents can also be used to increase the stability, particularly the thermal stability, of existing poliovirus vaccines or vaccines for related viruses. In addition, the agents can be used to prevent viral changes necessary for cell entry. The agents can also be used to terminate replication of live vaccine virus after sufficient time has elapsed to induce an immune response in an individual, minimizing the risk of vaccinees shedding reverted virus which are neurovirulent. The agents can additionally be used for prophylactic treatment of non-vaccinated family members of vaccinees. The agents can further be used for prophylaxis and therapeutic treatment of infection with enterovirus, Coxsackievirus, echoviruses, and other picornaviruses with accessible binding sites.

The ability of the agent to bind virus can be assessed by determining the MIC (minimum inhibitory concentration) value. The MIC value is found for these agents using standard methods (Andries, K. et al., *J. Virol.* 64:1117–1123 (1990)). Briefly, serial dilutions of the agent are added to solutions containing approximately 100 tissue culture infectious doses of viruses, and the resulting mixtures are added to subconfluent layers of HeLa cells in a microtiter plate. The MIC is taken as the lowest concentration of agent that protects 50% of cells from cytopathic effect (death).

Standard organic chemistry methods can be used to produce the agents of the current invention. For example, FIG. 21 depicts the molecules in the steps of the synthetic process for the agent depicted in FIG. 4, which is also the core region of Agents C and D. FIG. 22 depicts the molecules in the steps of the synthetic process for Agent C. The molecules added during the synthetic processes are depicted in FIGS. 23A and 23B. These molecules can be derived from known compounds; for example, the molecule shown in FIG. 23A can be derived from 5-hydroxyisophthalic acid (Aldrich #31,127-7). The molecule shown in FIG. 23B can be derived from DL-2-pyrrolidone- 5-carboxylic acid (Aldrich #29, 291-5) or from DL-glutamic acid; alternatively, it can be synthesized by the pathways shown in FIG. 23C. Standard reaction conditions are used (see, for example, March, *Advanced Organic Chemistry* (3d edition), Wiley & Sons, New York, N.Y. 1985); *Organic Syntheses*, Wiley & Sons, New York, N.Y. (annual volumes); Buehler and Pearson, *Survey of Organic Synthesis*, Wiley & Sons, New York, N.Y. (1970, 1977)). For alkylation of indoles in the 3-position by alcohols which can generate carbonium ions, see Hellman, H. et al., *Ann. Chem.* 604:214 (1957); under basic conditions, see Pratt, E. F. et al., *J. Am. Chem. Soc.* 79:5248 (1957), and Johnson, H. E., U.S. Pat. No. 3,197,479; see also Cardillo, B., et al., *Tetrahedron* 23:3771 (1967). For synthesis of an aminoalkylphenylenediamene, see Piotrovskii, L. B. et al., *Khim-Fram. Zh.* 9(10): 305 (1975). For synthesis of indoles substituted in the six-membered ring with β-aminoethyl groups, see Troxler, F. et al., *Helv. Chim. Acta* 51:1616 (1968). For synthesis of indoles substituted in the six-membered ring with formyl groups, see Backenberg, O. G. et al., *J. Chem. Soc.* 3961 (1962). Potential starting materials include: 5-hydroxy-isophthalic acid (Aldrich 31,127-8); 5-formylsalicylaldehyde (Aldrich 27,534-4) (4-hydroxyisophthalaldehyde); 5-formylsalicylic acid (Aldrich F1,760–1); DL-2-pyrrolidone-5-carboxylic acid (Aldrich 29,921-5); DL-glutamic acid (Aldrich G279–6); L-glutamic acid 5-methyl ester (Aldrich 85,829-9); and 5-cyanoindole (Aldrich C9,200-6) (5-indolecarbonitrile).

The invention is further illustrated by the following Examples, which are not to be considered limiting in any way.

EXAMPLE 1

Viral Structure and Virus/Agent Complex Structure

A. The structure of poliovirus and related picornaviruses

Poliovirus is a nonenveloped, icosahedral virus with a single-stranded, plus-sense RNA genome of approximately 7500 nucleotides enclosed in a roughly spherical protein capsid of approximately 310 Å in diameter and a maximum thickness of 50 Å. The viral capsid consists of 60 copies each of the viral proteins VP1, VP2, VP3, and VP4 for a total molecular weight of $8.5\times10^6$ daltons. The virus coat-proteins VP1, VP2, and VP3 are each eight-stranded wedge-shaped antiparallel β-barrels with two flanking helices, while VP4 is a short peptide. The immature particle is composed of the three viral proteins VP0, VP1 and VP3; during maturation, VP0 is cleaved to yield VP4 and VP2. In the mature particle, the viral proteins form a protomer unit with VP1, VP2, and VP3 packed together in pseudo T=3 positions and VP4 on the back side of the protomer inside the capsid. Protomers pack around the local five-fold axis to form pentamers and then twelve pentamers form the viral capsid. It is possible experimentally to isolate pentamers, and also empty capsids composed of VP0, VP1 and VP3.

The narrow end of the VP1 β-barrels packs around the five-fold axes, while the narrow ends of VP2 and VP3 alternate around the three-fold axes of the particle. Several prominent loops connecting the β-barrels of VP1, VP2 and VP3 are on the surface of the viral capsid and include residues identified as parts of antigenic sites (Emini, E. A., et al., *J. Virol.* 43:997 (1982); Crainic, R., et al., *Infect. Immun.* 41:1217 (1983); Minor, P. D., et al., *Nature* 301:674 (1983); Minor, P. D., et al., *J. Gen. Virol.* 65:1159 (1985); Ferguson, M., et al., *Virology* 143:505 (1985); and Diamond, D. C., et al., *Science* 229:1090 (1985)). Examination of the pentamer unit reveals a depression on the capsid surface or a "canyon" around the bottom of the β-barrels of the five symmetry-related copies of VP1, and it is proposed that cellular receptors bind to the virus in this canyon (Olson, N. H., et al., *Proc. Natl. Acad. Sci. USA* 90:507 (1993); and Hogle, J. M., *Cur. Biol.* 3:278 (1993)). At the base of the canyon there is an opening to a binding site within the β-barrel of VP1 that can accommodate various substituents. In all existing poliovirus structures there is electron-density in this binding pocket, and in the P1/Mahoney and P3/Sabin structures the density has been convincingly modeled as the lipid sphingosine. This is the same site that is occupied by the existing drugs, including the R (Janssen) and WIN (Sterling-Winthrop) compounds, in both poliovirus and in rhinovirus (Rossman, M. G., et al., *Nature* 317:145 (1985);

and Kim, K. H., et al., *J. Mol. Biol.* 230:206 (1993)). The native structures of rhinovirus 1A and 16 have a short-chain fatty acid modeled into the pocket, while the higher resolution rhinovirus 14 structure shows only four waters bound in the pocket (Smith, T. J., et al., *Science* 233:1286 (1986)). When the Sterling-Winthrop antiviral drug WIN 51711 binds to rhinovirus 14 (Smith, T. J., et al., *Science* 233:1286 (1986)), part of the "GH loop" (between β-strands G and H) in VP1 moves over 4 Å and partially "closes" the entrance to the pocket. This "trap-door" (residues 1232 to 1237 in poliovirus) is in essentially this same closed position in all poliovirus and rhinovirus structures that have either natural substituents or drugs in the binding pocket. In poliovirus, the carboxyl end of the GH loop of VP1 makes contact with the GH loop of VP3 which is near the protomer interface. Although early studies with rhinovirus 14 implicated the large conformational changes observed upon drug binding as being important in the antiviral activity of the Sterling-Winthrop "WIN" drugs, the lack of structural changes upon drug binding in rhinovirus 1A and rhinovirus 16, suggests an alternative mechanism in which occupation of the site interferes with conformational change associated with receptor binding (in rhinovirus 14 and 16).

Antiviral drugs prevent a variety of conformational transitions of the virus, including those necessary for productive cell entry (McSharry, J. J., et al., *Viroloqy* 97:307 (1979)) such as cell attachment and capsid uncoating, and therefore it seems likely that these drugs are exploiting a site that is normally used to regulate the stability of enteroviruses. Presumably the existing, partially effective drugs (such as the Sterling-Winthrop compound WIN 51711 and the Janssen compound R78206), displace the natural substituents because they have a higher binding constant and this tighter binding may prevent required rearrangements of the virus either by making the capsid too stable or by causing conformational changes upon binding that later interfere with cell attachment.

B. Existing virus/drug complex crystal structures

Several high resolution X-ray structures of drug complexes with poliovirus and rhinovirus exist (Zhang, A., et al., *Virology* 3:453 (1992)). They include the structures of P3/Sabin poliovirus complexed with each of the Janssen compounds R78206, R80633, and R77975; the mutant P3/Sabin poliovirus F1124L/F1134L (these binding site residues are Leu in the Mahoney strain) complexed with the Janssen compound R78206; and rhinovirus 14 complexed with a number of Sterling-Winthrop compounds and Janssen compounds (Zhang, A., et al., *Virology* 3:453 (1992)). The Janssen compounds differ only in the number of linker —$CH_2$ groups connecting the methyl-pyridozinyl piperidine group to the benzoate group. In all of the Janssen structures these drugs are oriented with the pyridazine group deepest in the pocket and the benzoate group nearest to the entrance. Similarly, the Sterling-Winthrop compound WIN 51711 is oriented so that the double ring, oxazoline group is deepest into the β-barrel and the isoxazoline group is near the entrance. In other Sterling-Winthrop WIN compounds, the occupancy of the drug binding site is reversed, such that the isoxazoline group is deepest into the β-barrel and the double ring is near the entrance. The occupancy of the Janssen compounds in the poliovirus binding site is greatest for R78206 (about 90%) and diminished for R80633 and again some for R77975.

EXAMPLE 2

Computational Agent Design

Most of the previously existing drugs for poliovirus and the related rhinovirus consist of two single, non-fused rings connected by a long chain to two additional single, non-fused, rings. In the preferred embodiment, new agents effective in early intervention against poliovirus and rhinovirus should have MIC values at least as low as those of the existing drugs. To determine which region of the virus structure defines the binding site and needs to be included in design calculations, the five drug complex structures described above, as well as the native P3/Sabin and P1/Mahoney poliovirus structures, were compared. Lists were compiled of all capsid residues within 4.5, 6, 8, 10, and 12.5 Å, respectively, of the substituent in the protomer 1 binding site in any of the six poliovirus structures described above. Several protomer 2 (which is related to protomer 1 by a 72° rotation about the five-fold axis) residues are near the protomer 1 binding site, and therefore must be considered in all agent design calculations.

A. Computational methodology used for agent design

As a first step in the design process, functional group maps of the P3/Sabin poliovirus binding site were made using the computer program MCSS (Miranker, A. and Karplus, M., *Proteins,* 11:29 (1991)). To prepare the protein coordinate set for the calculations, polar hydrogens were added to the P3/Sabin protomer using the hbuild command in CHARMM (Brooks, B. R., et al., *J. Comp. Chem.* 4:187 (1983)) and standard PARAM19 parameters and topology, and then a symmetry operation was applied to create the adjacent pentamer. The coordinate set was edited to include only those residues with atoms within 12.5 Å of the ligand in any of the six polio structures described above, plus five residues on either side of each of those residue ranges. It is necessary to excise part of the protein, because although the protein is fixed during an MCSS calculation, the number of protein atoms does significantly increase the CPU time required. The binding site is defined as an approximately $20\times20\times30$ Å$^3$ box that would enclose the sphingosine in protomer 1 of the native P3/Sabin poliovirus structure.

In a typical MCSS run, N copies of a given functional group were randomly distributed in the specified binding site, where N is usually between 1000 and 5000. Functional groups are typically simple small molecules. A large number of functional groups are available in the current implementation of MCSS, and additional functional groups can easily be included. The N copies of the group were then simultaneously, and independently, energy minimized in the field of the fixed protein, using a modified version of the program CHARMM. By the time-dependent Hartree approximation (Elber, R., et al., *J. Am. Chem. Soc.* 112:9161 (1990)), each copy felt the full force field of the protein but the copies did not interact with each other. More specifically, the N copies of the group were simultaneously subjected to 500 steps of steepest decent minimization followed by 500 steps of Powell minimization, and then nine cycles of 1000 steps of Powell minimization each, for a total of 10,000 minimization steps. After every 1000 steps of minimization, the functional group minima were gathered to remove duplicate minima. Minima were also deleted from the system after each cycle except for the first, if their interaction with the protein energy was too high as determined by a series of user specified energy cutoffs. After the final cycle, the remaining minima were sorted by interaction energy and their coordinates and interaction energy were written to a file. Since the protein competes with solvent for binding functional groups, only minima whose free energy of binding to the protein was less than their free energy of solvation were considered. In the Born approximation, one half of the enthalpy of solvation is equal to the free energy of solvation for charged ions, (Roux, B., et al., *J. Phys. Chem.* 94:4683

(1990)) and therefore for charged and polar functional groups only minima with an interaction energy less than one half their solvation enthalpy were examined. Numerous test calculations were performed mapping the group N-methyl acetamide into the P3/Sabin binding site, to determine the set of protein residues, number of copies of a group, and distance-to-protein cutoff for the initial distribution of the copies, and gather cutoffs to use for the final series of MCSS calculations with various functional groups.

B. Mapping various functional groups into the P3/Sabin poliovirus binding site

Several polar, charged, aromatic, and aliphatic functional groups have been mapped into the P3/Sabin poliovirus binding site, including N-methyl acetamide, methanol, water, acetic acid, methyl-ammonium, unhydrated $Mg^{2+}$, $MG^{2+}$... $H_2O$ (treated as one functional group), the tryptophan sidechain, the histidine sidechain, phenol, benzene, the phenylalanine sidechain, cyclohexane, propane, and isobutane. For this protein the cpu time required to minimize 1000 group copies ranged from about 11 hours for a small group like methyl-ammonium to about 60 hours for a large group like the tryptophan sidechain on a singe SGI R3000 processor. These calculations predicted that a pattern of double six-membered (or five- and six-membered fused) aromatic ring connected to a single six-membered aromatic ring connected to a double ring again should preferentially bind in the P3/Sabin poliovirus binding site. Also, a side-pocket at the protomer-protomer interface was identified as a possible alternative drug binding site. The results showed that this side-pocket, which branches off the center of the main binding pocket, could accommodate a ligand with net positive charge.

C. Clustering and connecting functional group minima

Figure 14:
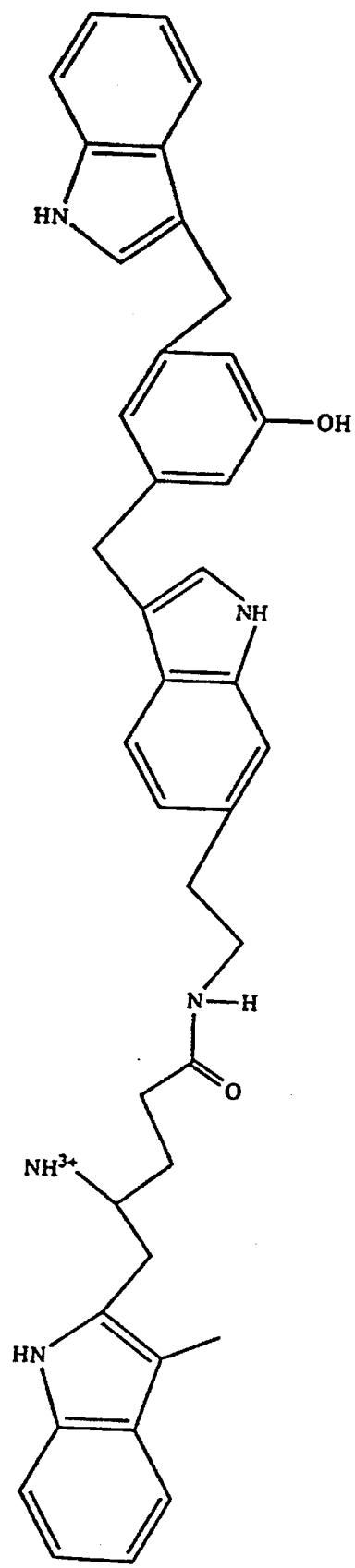
FIG. 14 is a depiction of an agent of the current invention, designated Agent A.
Figure 15:
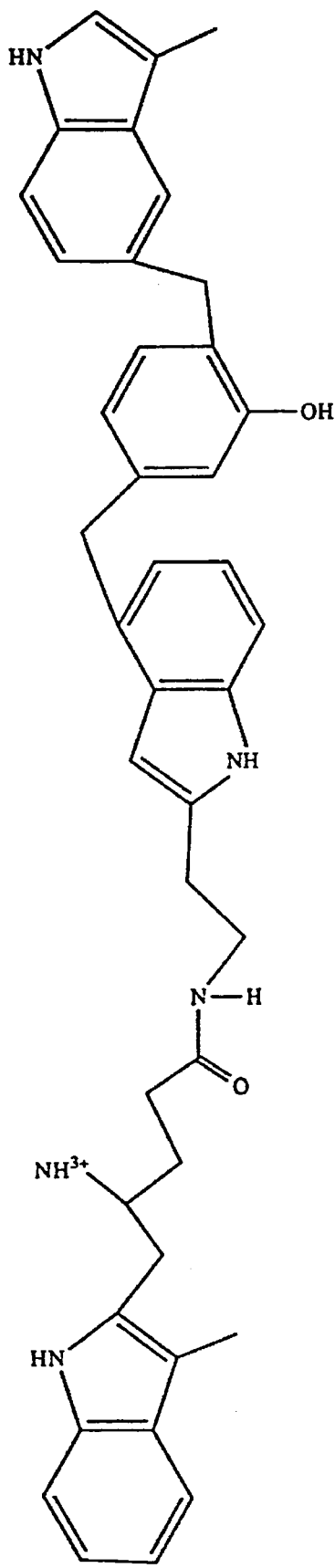
FIG. 15 is a depiction of an agent of the current invention, designated Agent B.
Figure 16:
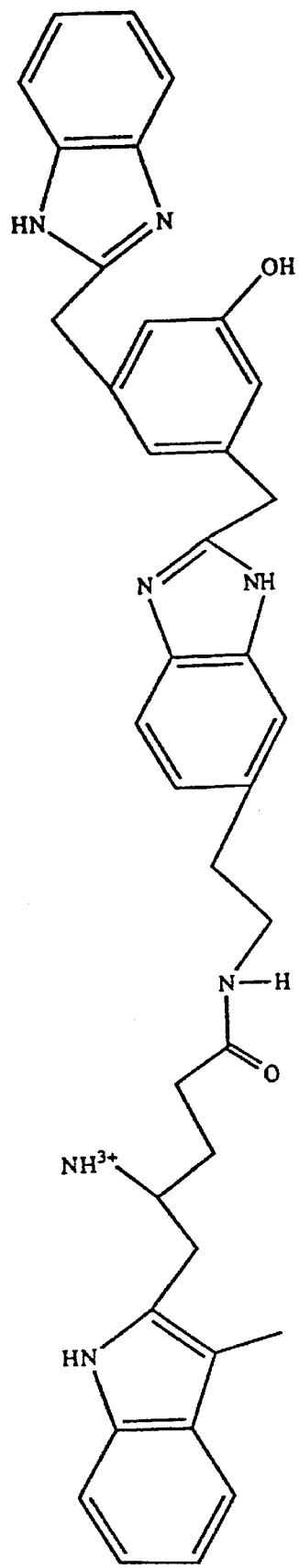
FIG. 16 is a depiction of an agent of the current invention, designated Agent C.
Figure 17:
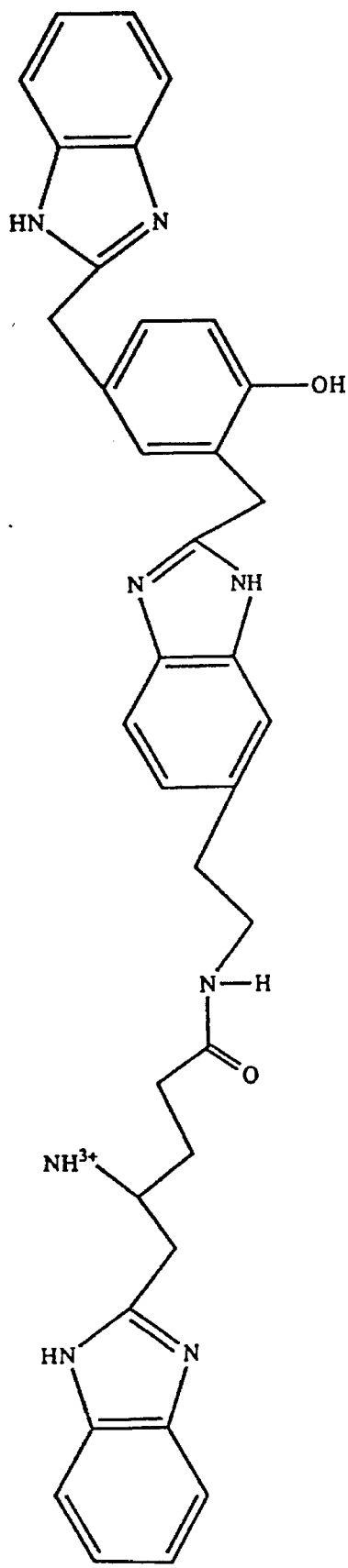
FIG. 17 is a depiction of an agent of the current invention, designated Agent D.
Figure 18:
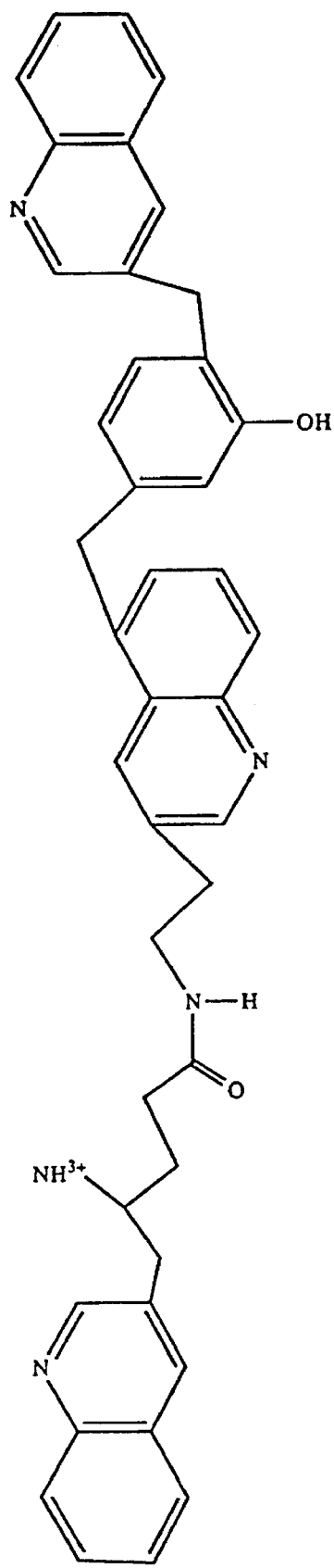
FIG. 18 is a depiction of an agent of the current invention.
Figure 19:
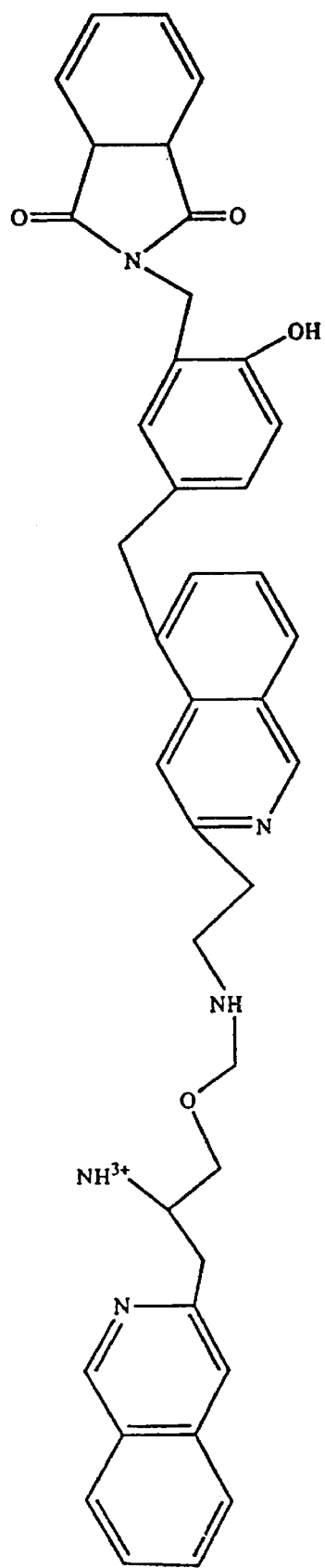
FIG. 19 is a depiction of an agent of the current invention.
Figure 20:
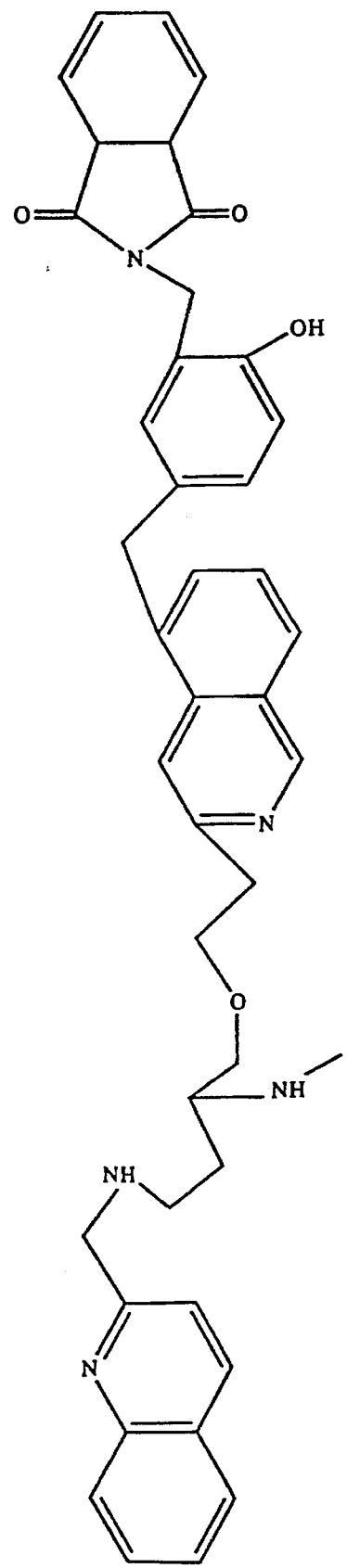
FIG. 20 is a depiction of an agent of the current invention.
Figure 21:
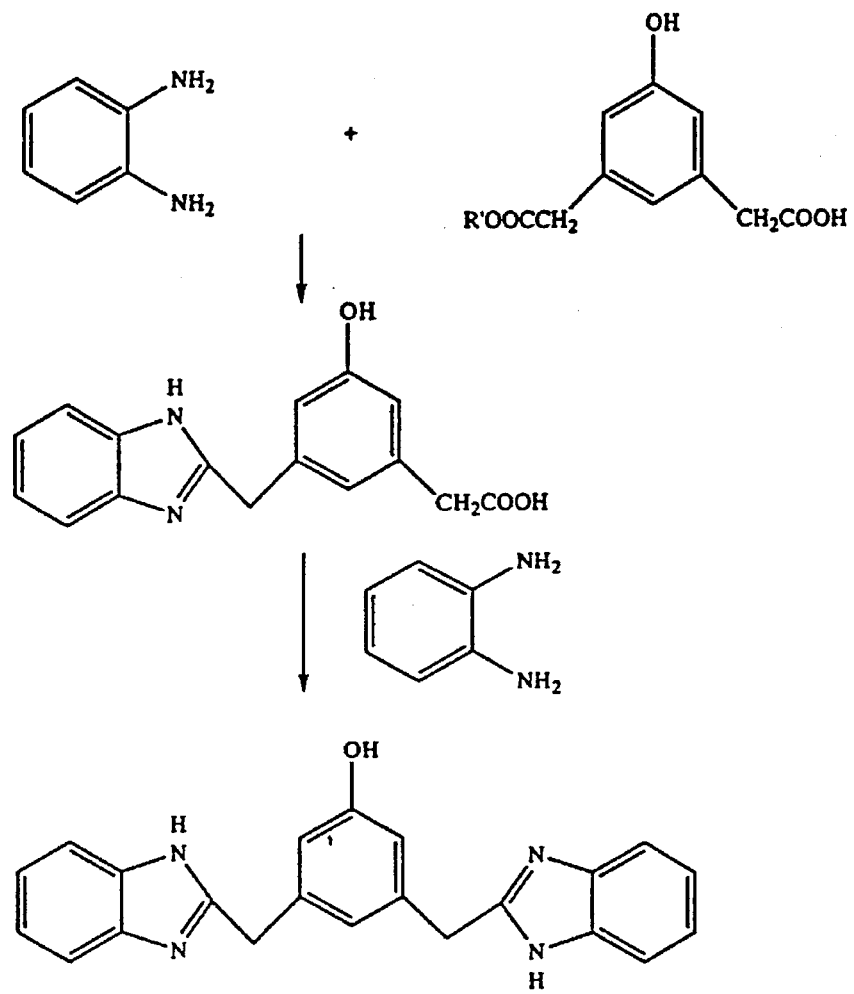
FIG. 21 is a schematic diagram of the synthetic process for the agent depicted in FIG. 4.
Figure 22:
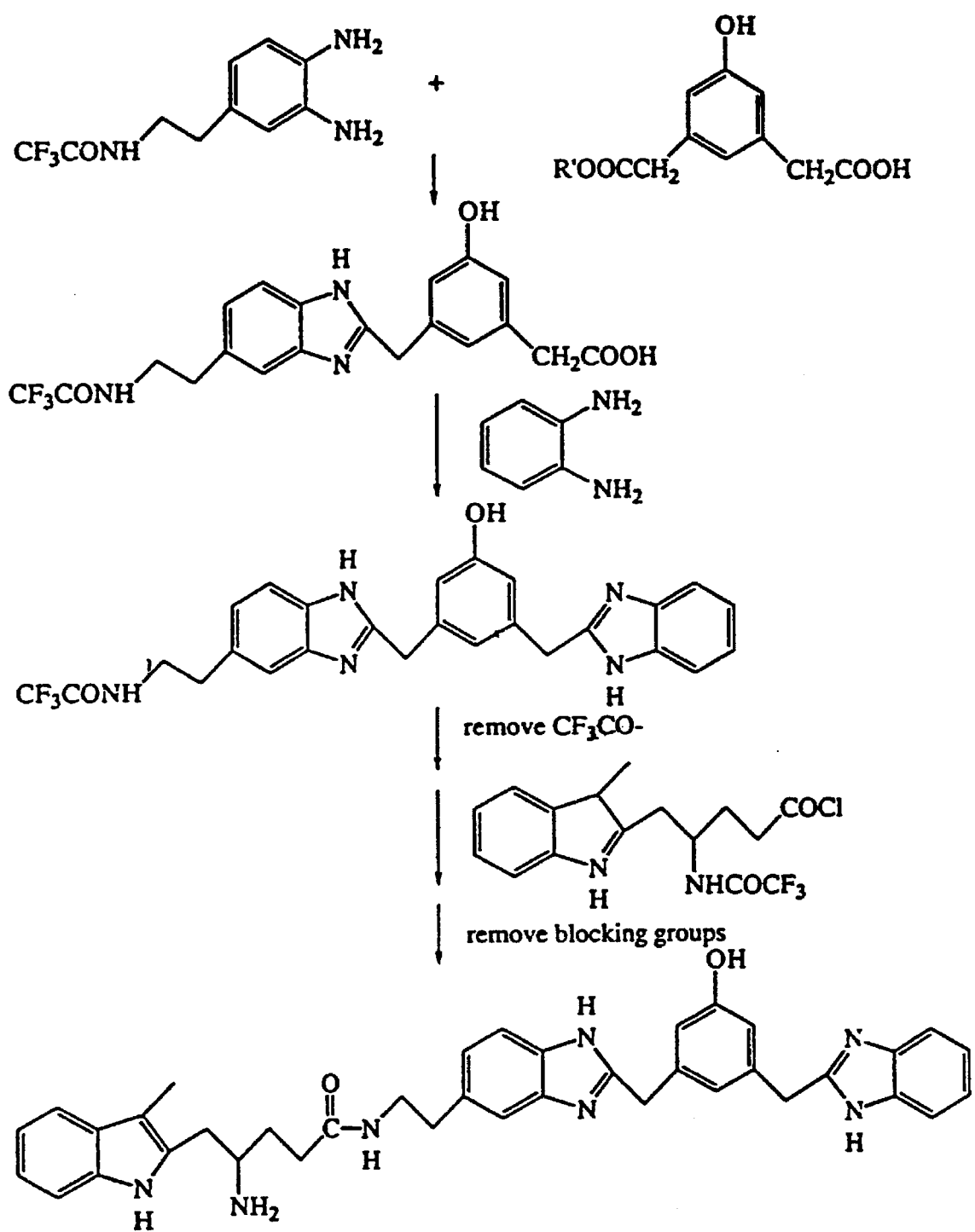
FIG. 22 is a schematic diagram of the synthetic process for Agent C, depicted in FIG. 16.
Figure 23A:
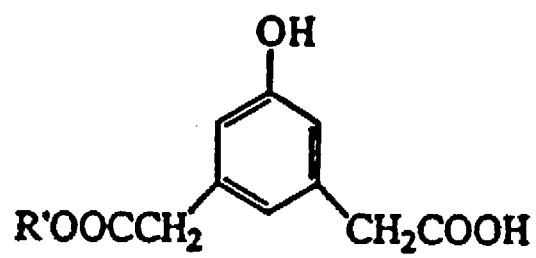
FIG. 23A and FIG. 23B are depictions of the molecules added during the synthetic processes shown in FIGS. 21 and 22.
Figure 23B:
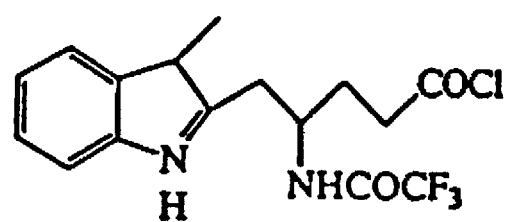
Figure 23C:
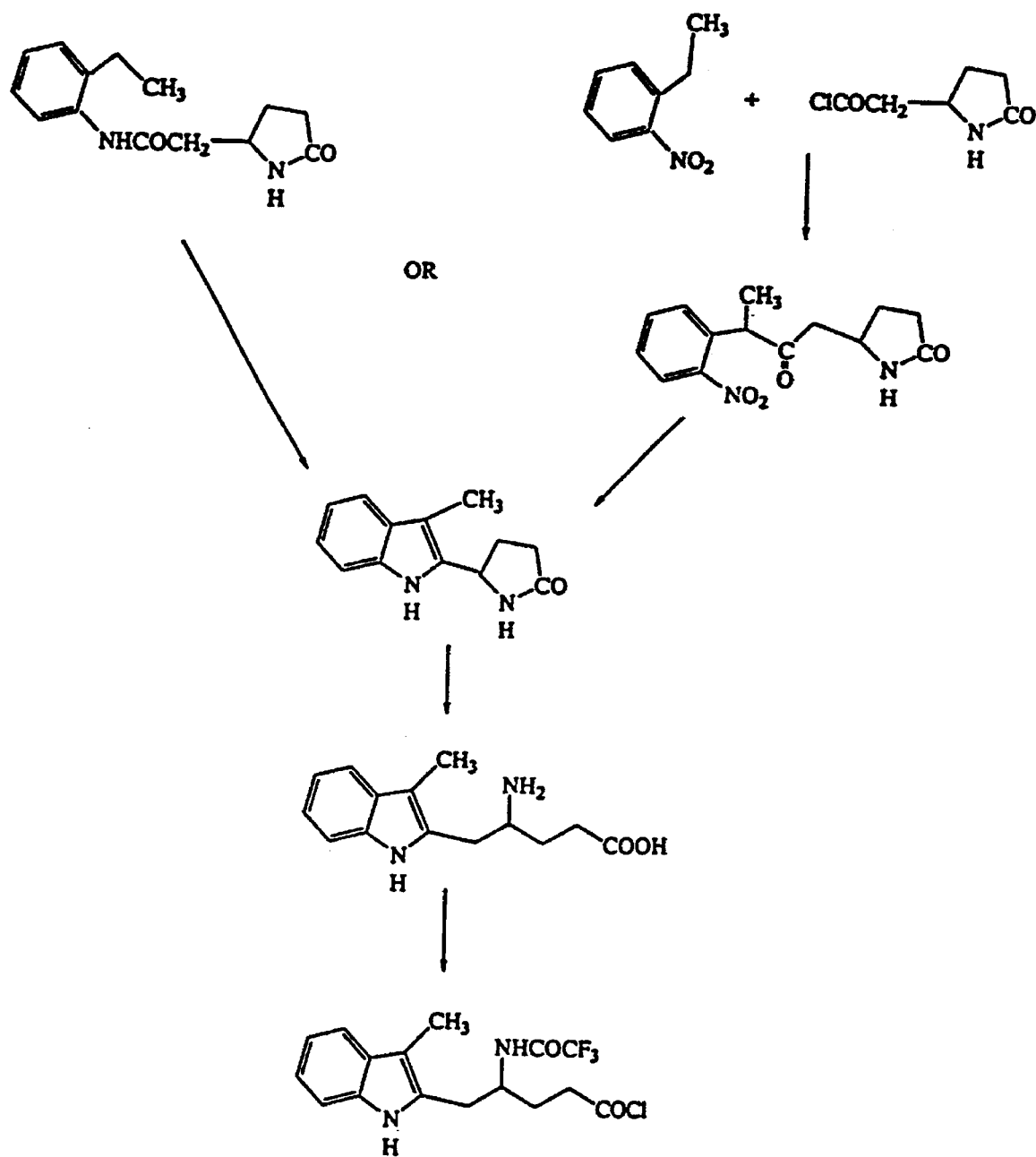
FIG. 23C is a schematic diagram of a synthetic process for the molecule shown in FIG. 23B.
Figure 24:
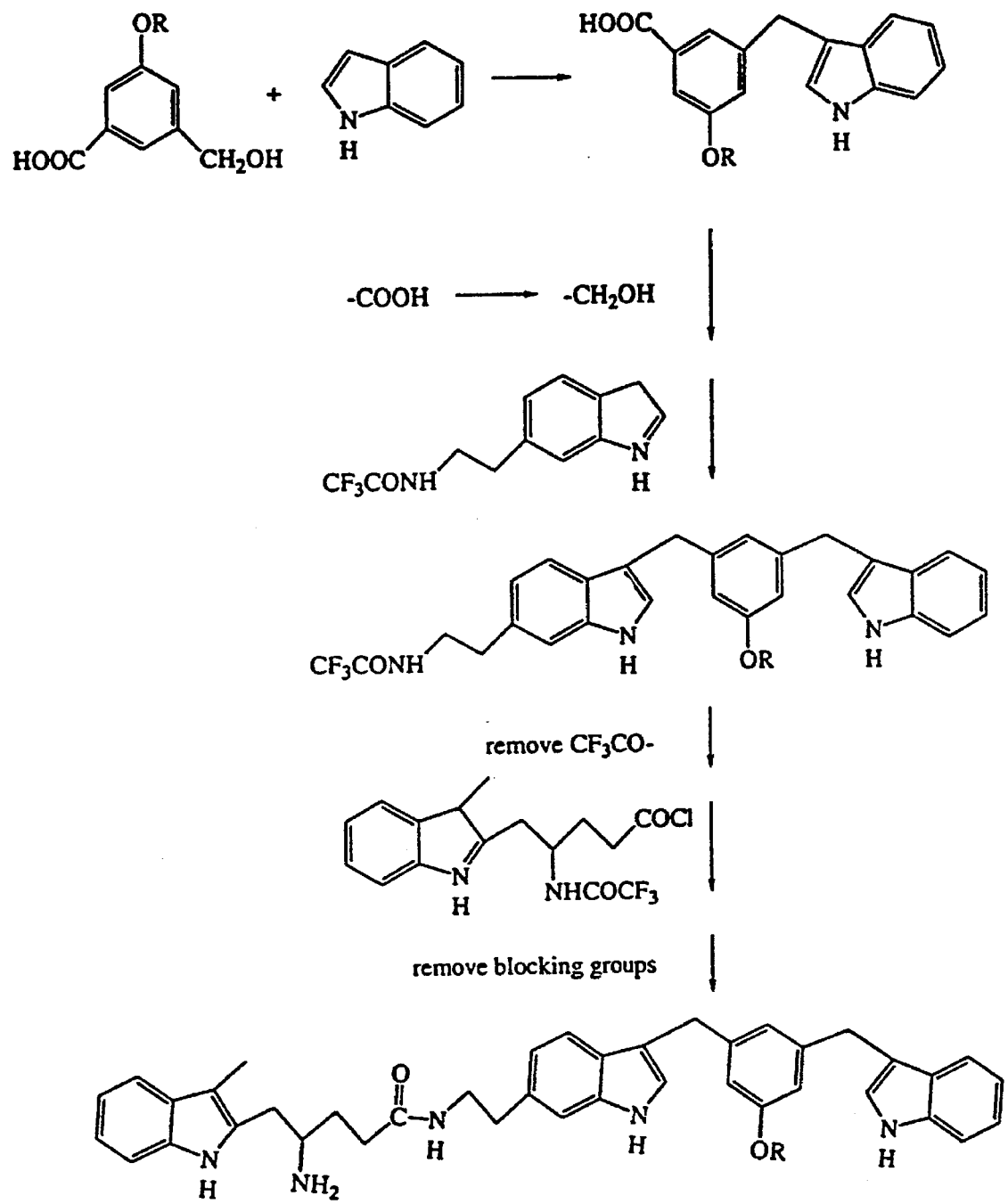
FIG. 24 is a schematic diagram for the synthetic process for Agent A, depicted in FIG. 14, in which R is hydrogen.

After mapping the various functional groups into the binding site, the minima were clustered by inspection and a few of the best (lowest energy) minima were selected from each cluster. A set of these minima was then connected by placing linker —$CH_2$ groups between the minima where necessary to create a chemically sensible molecule. First, the linker atoms were minimized and annealed in the fixed protein with a minima also fixed in their MCSS positions. Then, the entire newly designed agent molecule was minimized in the fixed protein. Finally, the agent molecule and the protein were minimized together, and later the interaction energy of the minimized agent with the fixed protein was calculated. Through this process, two new agent molecules were designed; these are shown in FIGS. 14 and 15. To facilitate synthesis, Agent A was modified and Agents C and D were modeled through the process described above. Energy minimizations of the agent/virus complexes suggest that the agents will bind at least as strongly as the best of the currently known compounds. All four agents have significantly lower interaction energy with the protein than the Janssen compound R78206; these results are summarized in Table 1, below.

TABLE 1

| | Interaction Energy of Agents[1] | | | |
|---|---|---|---|---|
| | Total of mcss minima[2] | Agent with links optimized in fixed protein (vdw and elec[2]) | Agent minimized in fixed protein (vdw and elec[2]) | Agent minimized with protein (vdw and elec[2]) |
| Agent A | (−166.6) | 305.4 (41.0) | −57.8 (−117.5) | −121.7 (−181.8) |

TABLE 1-continued

| | Interaction Energy of Agents[1] | | | |
|---|---|---|---|---|
| | Total of mcss minima[2] | Agent with links optimized in fixed protein (vdw and elec[2]) | Agent minimized in fixed protein (vdw and elec[2]) | Agent minimized with protein (vdw and elec[2]) |
| Agent B | (−167.5) | 1657.5 (1400.5) | −22.2 (−106.6) | −104.0 (−180.1) |
| Agent C | — | 458.1 (96.9) | −58.6 (−124.0) | −136.6 (−197.4) |
| Agent D | — | 669.8 (268.9) | −68.6 (−130.5) | −136.5 (−191.1) |
| R78206 | — | — | −4.0 (−35.9) | −40.2 (−66.0) |

[1]All energies are in kcal/mol and include the internal energy terms of the drug unless otherwise stated.
[2]Includes van der Waals (vdw) and electrostatic (elec) energy terms only.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A compound, wherein the compound is represented by a structure selected from the group consisting of:

wherein R is —H or —OH.

* * * * *